United States Patent [19]

Dean et al.

[11] Patent Number: 5,424,448
[45] Date of Patent: Jun. 13, 1995

[54] PREPARATION OF CARBONIC ANHYDRASE INHIBITORS

[75] Inventors: William D. Dean, Arlington; Paul W. Zinke; Steven J. Sproull, both of Fort Worth; Michael E. Deason, Burleson; Raymond E. Conrow; Anura P. Dantanarayana, both of Fort Worth, all of Tex.

[73] Assignee: Alcon Laboratories, Inc., Fort Worth, Tex.

[21] Appl. No.: 182,916

[22] Filed: Jan. 14, 1994

Related U.S. Application Data

[62] Division of Ser. No. 19,012, Feb. 18, 1993, Pat. No. 5,344,929.

[51] Int. Cl.$^6$ ............... C07D 333/34; C07D 333/28; C07D 333/22
[52] U.S. Cl. ...................... 549/64; 549/81; 549/73; 549/70; 549/65
[58] Field of Search ............... 549/62, 64, 71, 83, 549/65, 67, 81, 70

[56] References Cited

U.S. PATENT DOCUMENTS

| | | | |
|---|---|---|---|
| 2,579,494 | 12/1951 | Hermann | 549/73 |
| 2,746,973 | 5/1956 | Gregory et al. | 549/64 |
| 4,723,988 | 2/1988 | Shapiro | 544/219 |
| 4,867,781 | 9/1989 | Pasteris et al. | 544/49 |
| 4,918,246 | 4/1990 | Brown | 568/812 |
| 4,929,637 | 5/1990 | Baldwin et al. | 514/445 |
| 5,177,074 | 1/1993 | Allen et al. | 514/234.5 |

FOREIGN PATENT DOCUMENTS

WO91/15486 10/1991 WIPO.

OTHER PUBLICATIONS

Kühle, Engelbert, "One Hundred Years of Sulfenic Acid Chemistry. Sulfenyl Halide Syntheses," *Synthesis*, No. 11, 561–571, (1970).

Baker, et al., "The Cleavage of Organic Sulfides with Chlorine," J.A.C.S., vol. 68, 2636–2639, (1946).

Kwart, et al., "Chlorinolysis of Sulfur–Carbon Bonds in Aryl–Alkyl Sulfides," J.A.C.S., vol. 78, 5008–5011, (1956).

Douglass, et al., "The Interaction of Chlorine with Different Types of Organic Sulfur Compounds," J.A.C.S., vol. 60, 1486–1488, (1938).

Brown et al., "Selective Reductions. 40. A Critical Examination of the Relative Effectiveness of Various Reducing Agents for the Asymmetric Reduction of Different Classes of Ketones," *J. Org. Chem.*, 1987, 52, 5406–5412.

Graham et al., "The Reaction of Sulfinic Acid Salts with Hydroxylamine-O-sulfonic Acid. A Useful Synthesis of Primary Sulfonamides," *Synthesis*, Dec., 1986, 1031–1032.

*Primary Examiner*—Richard L. Raymond
*Assistant Examiner*—Deborah Lambkin
*Attorney, Agent, or Firm*—Sally Yeager

[57] ABSTRACT

A process for synthesizing carbonic anhydrase inhibitors is disclosed.

2 Claims, No Drawings

PREPARATION OF CARBONIC ANHYDRASE INHIBITORS

This is a divisional of U.S. patent application Ser. No. 08/019,012 filed Feb. 18, 1993, U.S. Pat. No. 5,344,929.

This invention is directed to a process for synthesizing carbonic anhydrase inhibitors which are useful in the control of ocular hypertension. The invention also relates to novel intermediate compounds, which are integral to the claimed process.

BACKGROUND OF THE INVENTION

Certain (R)-3,4-dihydro-4-alkylamino-2-substituted-2H-thieno[3,2-e]-1,2-thiazine-6-sulfonamide-1,1-dioxides of the structural formula I (shown below) have previously been prepared by resolution of the racemate via the di-p-toluoyl-D-tartaric acid salt or from (S)-3,4-dihydro-4-hydroxy-2-substituted-2H-thieno[3,2-e]-1,2-thiazine-6-sulfonamide-1,1-dioxides by activation of the C(4)-hydroxyl group and displacement with the appropriate amine. Both of these methods, as well as a process for the preparation of the requisite (S)-3,4-dihydro-4-hydroxy-2-substituted-2H-thieno[3,2-e]-1,2-thiazine-6-sulfonamide-1,1-dioxides from 3-acetylthiophene, are disclosed by Dean et al. in PCT/U.S. Ser. No. 91/02262. The present invention provides an improved process for the preparation of (R)-3,4-dihydro-4-alkylamino-2-substituted-2H-thieno[3,2-e]-1,2-thiazine-6-sulfonamide-1,1-dioxides from 3-acetyl-2,5-dichlorothiophene.

SUMMARY OF THE INVENTION

The present invention provides a process for the synthesis of (R)-3,4-dihydro-4-alkylamino-2-substituted-2H-thieno[3,2-e]-1,2-thiazine-6-sulfonamide-1,1-dioxides of the structural formula I from 3-acetyl-2,5-dichlorothiophene:

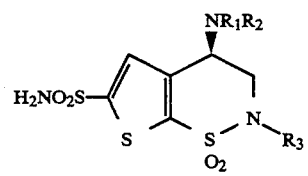

I wherein: $R_1$ and $R_2$ are both chosen from H or $C_{1-4}$ alkyl; $R_3=C_{1-6}$ alkyl, $CH_2(CH_2)_nOR_4$ where $R_4=CH_3$ or $(CH_2)_nCH_3$ and $n=1-4$; or $(CH_2)_nAr$ where Ar=unsubstituted phenyl, 3-methoxyphenyl, or 4-methoxyphenyl and $n=1$ or 2.

The reaction scheme can be summarized as involving the following steps:

Step 1 Thioether formation

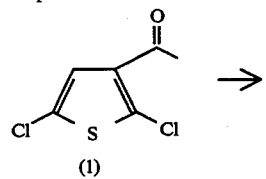

Step 2 Sulfonamide formation

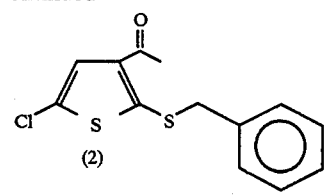

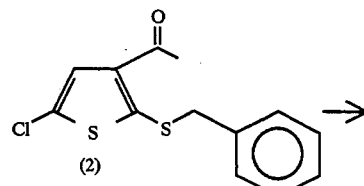

Step 3 Bromination

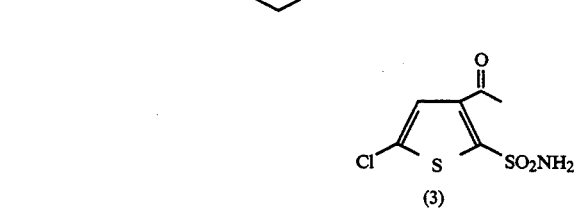

Step 4 Asymmetric reduction/cyclization

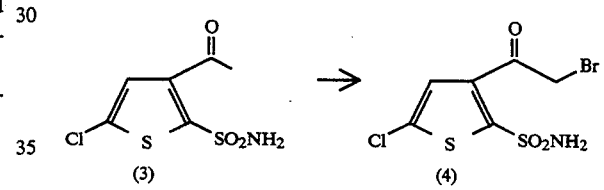

Step 5 N(2) Alkylation

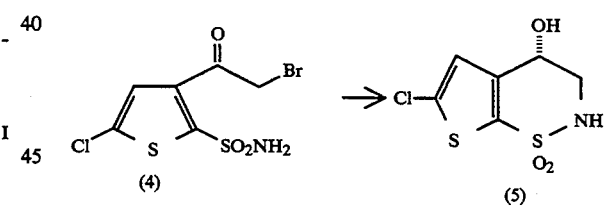

Step 6 C(6) Halogen-metal exchange/sulfamoylation

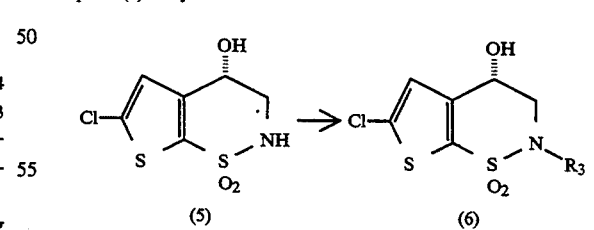

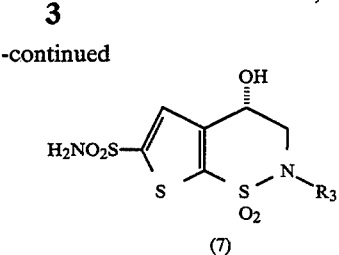

(7)

Step 7 C(6)-Sulfonamide protection/C(4)-hydroxyl activation/displacement

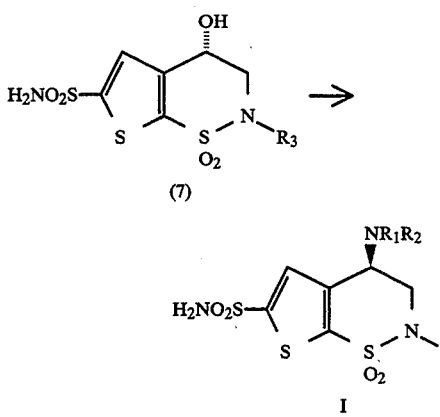

The process comprises displacing the C(2)-chloro of 3-acetyl-2,5-dichlorothiophene (1) with benzyl mercaptide to form the thioether of structure (2), which is then converted to 3-acetyl-5-chloro-2-thiophenesulfonamide (3) by reaction with chlorine to form 3-acetyl-5-chloro-2-thiophenesulfenyl chloride, followed by reaction with ammonia to form 3-acetyl-5-chloro-2-thiophenesulfenamide, and finally oxidation. Bromination provides 3-bromoacetyl-5-chloro-2-thiophenesulfonamide (4), which is converted to (S)-3,4-dihydro-6-chloro-4-hydroxy-2H-thieno[3,2-e]-1,2-thiazine-1,1-dioxide (5) by reduction with (+)-β-chlorodiisopinocampheylborane followed by treatment with aqueous base. Alkylation at N(2) provides the (S)-3,4-dihydro-6-chloro-4-hydroxy-2-substituted-2H-thieno[3,2-e]-1,2-thiazine-1,1-dioxide of structure (6). Formation of the C(6) anion is accomplished by halogen-metal exchange, and the anion is reacted with sulfur dioxide to form a lithium sulfinate, which upon reaction with hydroxylamine-O-sulfonic acid provides the (S)-3,4-dihydro-4-hydroxy-2-substituted-2H-thieno[3,2-e]-1,2-thiazine-6-sulfonamide-1,1-dioxide of structure (7). Protection of the C(6)-sulfonamide functionality, followed by activation of the C(4)-hydroxyl and displacement with an appropriate amine provides the (R)-3,4-dihydro-4-alkylamino-2-substituted-2H-thieno[3,2-e]-1,2-thiazine-6-sulfonamide-1,1-dioxide of structure I.

DETAILED DESCRIPTION OF THE INVENTION

The present invention eliminates some of the problems inherent in the prior art when it is desirable to produce the carbonic anhydrase inhibitors of structure I in commercial quantities. Specifically, this improvement eliminates the need for chromatographic purification of intermediates and provides the (R)-3,4-dihydro-4-alkylamino-2-substituted-2H-thieno[3,2-e]-1,2-thiazine-6-sulfonamide-1,1-dioxides in higher overall yield.

In words relative to the above schematic representations, the synthesis of (R)-3,4-dihydro-4-alkylamino-2-substituted-2H-thieno[3,2-e]-1,2-thiazine-6-sulfonamide-1,1-dioxides is described in greater detail below.

In the initial step of the process, commercially available 3-acetyl-2,5-dichlorothiophene (1) is converted to a thioether, such as 3-acetyl-5-chloro-2-(benzylthio)thiophene (2), by reaction with a mercaptide in a two solvent system consisting of water and tetrahydrofuran or a lower alkyl alcohol. In principle, any lower alkyl mercaptide would suffice; however, benzyl mercaptide is preferred. The reagent is generated in situ either by treatment of benzyl mercaptan with aqueous sodium hydroxide or by treatment of the pseudourea obtained by reaction of thiourea with a benzyl halide, such as benzyl chloride, with aqueous sodium hydroxide. Use of the latter method in ethanol, at a temperature of 45° to 85° C., for a period of 2 to 6 hours is preferred. The product is precipitated by dilution with water and cooling to room temperature. After residual mercaptan is destroyed by exposure to sodium hypochlorite, the material is conveniently collected by filtration.

The second step of the process comprises the conversion of 3-acetyl-5-chloro-2-(benzylthio)thiophene (2) to 3-acetyl-5-chloro-2-thiophenesulfonamide (3). This can be accomplished by oxidative chlorination using chlorine in dilute aqueous acetic or hydrochloric acid followed by treatment with ammonium hydroxide or, preferably, by a 3-stage process that proceeds via the intermediate sulfenyl chloride and sulfenamide. The first stage of the preferred process consists of conversion of 2 to the intermediate 3-acetyl-5-chloro-2-thiophenesulfenyl chloride by treatment with sulfuryl chloride or, preferably, chlorine in a solvent such as carbon tetrachloride, ethyl acetate, or toluene at a temperature of −10° to 15° C. for 30 minutes to an hour. While the sulfenyl chloride can be isolated in high yield by solvent removal when the reaction is performed in carbon tetrachloride, it is preferrable to perform the reaction in ethyl acetate and to use the suspension directly in the second stage. The second stage consists of conversion of the intermediate sulfenyl chloride to the intermediate 2-thiophenesulfenamide by reaction with ammonia. The suspension of the sulfenyl chloride is first purged with air or nitrogen to remove excess chlorine and then ammonium hydroxide or, preferrably, anhydrous ammonia is added at a temperature of 0° to 15° C. The reaction is usually complete in 30 minutes to 1 hour. The third stage consists of oxidation of the intermediate 2-thiophenesulfenamide to the 2-thiophenesulfonamide (3). This can be accomplished using either m-chloroperbenzoic acid in a two-phase system consisting of toluene and aqueous sodium bicarbonate or, preferably, 0.1 to 0.5 equivalents of sodium tungstate dihydrate in a two-phase system consisting of aqueous hydrogen peroxide and ethyl acetate at a temperature of 0° to 45° C. for a period of 2 to 24 hours. The sulfonamide is isolated by phase separation, a wash with bisulfite solution to destroy excess peroxide, and solvent removal.

The third step of the process is bromination of 3-acetyl-5-chloro-2-thiophenesulfonamide (3) to provide 3-bromoacetyl-5-chloro-2-thiophenesulfonamide (4). This can be accomplished using pyridinium bromide perbromide and an acid catalyst such as hydrogen chloride, hydrogen bromide, or sulfuric acid in tetrahydrofuran, ethyl acetate, or a lower alkyl alcohol. Alternatively, this can be accomplished using bromine and sulfuric acid in methanol at a temperature of 0° to 20° C. over a period of 1 to 6 hours. When the brominating agent is pyridinium bromide perbromide, the preferred method utilizes sulfuric acid and ethyl acetate. After the bromination is complete, the ethyl acetate solution is washed with water to neutrality and the product is isolated by solvent removal and trituration. The material obtained, typically contaminated with less than 10% of the dibromoketone, is acceptable for use in step 4.

In the fourth step of the process, 3-bromoacetyl-5-chloro-2-thiophenesulfonamide (4) is reduced with an appropriate reagent to provide initially an (S)-bromohydrin, which upon subsequent treatment with aqueous sodium hydroxide cyclizes to (S)-3,4-dihydro-6-chloro-4-hydroxy-2H-thieno[3,2-e]-1,2-thiazine-1,1-dioxide (5). The preferred reducing agent is (+)-β-chlorodiisopinocampheylborane, which is well known to provide bromohydrins in high enantiomeric excess from prochiral α-bromo ketones [H. C. Brown, W. S. Park, B. T. Cho, and P. V. Ramachandran *J. Org. Chem.* 52, 5406 (1987) and H. C. Brown U.S. Pat. No. 4,918,246 (1990)]. Several different reaction solvents can be used for the reduction of (4), including diethyl ether, tetrahydrofuran, and t-butyl methyl ether. The reduction is typically carried out using 1.2 to 2.2 equivalents of (+)-β-chlorodiisopinocampheylborane at a temperature of −40° to 0° C. for 6 to 24 hours. A higher enantiomeric excess is obtained at the lower temperature; however, the reaction rate is slower. The preferred conditions utilize t-butyl methyl ether at a temperature of −25° to −15° C. After the reduction is complete, aqueous potassium or sodium hydroxide is added and the mixture is stirred at ambient temperature for a period of 1 to 5 hours to accomplish cyclization. The product is isolated by phase separation, acidification of the aqueous phase, extraction, solvent removal, and trituration. The enantiomeric excess of the (5) produced is typically greater than 96%.

The fifth step of the process is alkylation of (5) at N(2) with the appropriate alkylating agent to produce the (S)-3,4-dihydro-6-chloro-4-hydroxy-2-substituted-2H-thieno[3,2-e]-1,2-thiazine-1,1-dioxide of structure (6). This can be accomplished using an alkyl halide (eg. chloride, bromide, or iodide), tosylate, or mesylate and a base/solvent combination such as sodium hydride in dimethylformamide, potassium carbonate in acetonitrile or dimethylsulfoxide, or in a two phase system using a phase transfer catalyst. The most convenient and preferred method utilizes the alkyl halide and potassium carbonate in dimethylsulfoxide at 25° to 40° C. for a period of 18 to 24 hours. Upon completion, the reaction is diluted with saturated aqueous sodium chloride and the product is isolated by extraction using diethyl ether or, preferably, t-butyl methyl ether and solvent evaporation. The material obtained is of sufficient quality that it can be used in the next step without further purification.

The sixth step of the process comprises the conversion of the C(6)-chloro atom of an (S)-3,4-dihydro-6-chloro-4-hydroxy-2-substituted-2H-thieno[3,2-e]-1,2-thiazine-1,1-dioxide of structure (6) to a sulfonamide functionality, providing an (S)-3,4-dihydro-4-hydroxy-2-substituted-2H-thieno[3,2-e]-1,2-thiazine-6-sulfonamide-1,1-dioxide of structure (7). One way of accomplishing this is to treat 6 with an alkyllithium to form a C(6) anion which, by reaction with sulfur dioxide, followed by treatment with chlorine, N-chlorosuccinimide, or a similar source of positive halogen, followed by treatment with ammonia, provides 7. In the preferred method, the C(6) anion is formed by halogen-metal exchange using 2 to 2.5 equivalents of an alkyllithium such as n-, s-, or t-butyllithium in a solvent such as dimethoxyethane or tetrahydrofuran at a temperature of −78° to −20° C. The use of n-butyllithium as a hexane solution and tetrahydrofuran as the reaction solvent is most convenient. In the second stage, the C(6) anion is reacted with sulfur dioxide to form an intermediate lithium sulfinate. This is accomplished by simply passing sulfur dioxide into or over the −78° to −20° C. solution of the anion until the pH of the mixture is about 4. In the third stage, the solvent is removed, and the solid lithium sulfinate is converted to the sulfonamide using the method of S. L. Graham and T. H. Scholtz *Synthesis*, 1031 (1986). This is accomplished by adding an aqueous solution of the lithium sulfinate to a 0° to 25° C. solution of 5 to 10 equivalents of sodium acetate and 3 to 6 equivalents of hydroxylamine-O-sulfonic acid in water. After a reaction time of 6 to 18 hours, the product is isolated by extraction into ethyl acetate, solvent removal, and trituration.

The seventh step of the process is conversion of the (S)-3,4-dihydro-4-hydroxy-2-substituted-2H-thieno[3,2-e]-1,2-thiazine-6-sulfonamide-1,1-dioxide of structure (7) to a (R)-3,4-dihydro-4-alkylamino-2-substituted-2H-thieno[3,2-e]-1,2-thiazine-6-sulfonamide-1,1-dioxide of structure I. This is accomplished in three stages consisting of a) protection of the C(6)-sulfonamide functionality as a lower alkoxyimidate, b) activation of the C(4)-hydroxyl group, and c) displacement of the activated C(4)-hydroxyl group with the appropriate amine with inversion of the stereochemistry at C(4) and removal of the protecting group from the C(6)-sulfonamide functionality. Protection of the C(6)-sulfonamide functionality minimizes subsequent sulfonimide formation during activation of the C(4)-hydroxyl group. Protection is accomplished by refluxing a solution of (7) and an excess of a lower alkyl orthoacetate, such as trimethyl orthoacetate, in acetonitrile for a period of 12 to 48 hours. After solvent removal, stage two is carried out by replacing the solvent with tetrahydrofuran and reacting the C(4)-hydroxyl group with methanesulfonic anhydride or a sulfonyl chloride such as p-toluenesulfonyl chloride, p-bromotoluenesulfonyl chloride, or p-nitrotoluenesulfonyl chloride in the presence of a base such as pyridine, triethylamine, or dimethylaminopyridine. Two to 2.5 equivalents of p-toluenesulfonyl chloride and triethylamine at a temperature of −10° to 15° C. for a period of 1 to 4 hours are preferred. When tosylation is complete, stage three is accomplished by adding 10 to 40 equivalents of the appropriate amine to the cold solution. After a period of 8 to 60 hours, the product is isolated by an acid-base workup.

The synthesis of the present invention is further illustrated by the following examples, wherein specific embodiments of the invention are described in detail. However, it should be understood that the invention is not limited to the specific details of these examples.

EXAMPLE 1

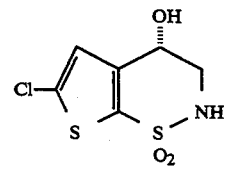

(S)-3,4-Dihydro-6-chloro-4-hydroxy-4H-thieno[3,2-e]-1,2-thiazine-1,1-dioxide (5)

Step 1. 3-Acetyl-5-chloro-2-(benzylthio)thiophene (2)

A mixture consisting of thiourea (1.287 kg, 16.93 mol), benzyl chloride (1.858 L, 2.044 kg, 16.14 mol), ethanol (13.5 L), and water (4.5 L) was heated to reflux over 2 hours. The mixture was allowed to cool to 74° C. over 20 minutes before 3-acetyl-2,5-dichlorothiophene (1) (3.0 kg, 15.38 mol) was added followed by 4M aqueous sodium hydroxide (10 L). The mixture was returned to reflux and maintained there for 3 hours, after which TLC analysis indicated complete reaction. After the mixture had cooled to room temperature overnight, water (10 L) was added, and the mixture was stirred for 30 minutes before bleach (3 L of 5.25% sodium hypochlorite) was added. After stirring for another 30 minutes, the solid was collected by filtration, washed with water (4×2.5 L) and 2-propanol (3×2 L), and dried in air at ambient temperature to a constant weight of 4.224 kilograms (97%) of 2: mp 86°–88° C.; IR (KBr) 1648, 1507, 1496, 1405, 1227, 1042, 830, 714, 696, 482 cm$^{-1}$; $^1$H NMR (CDCl$_3$) $\delta$7.34-7.25 (m, 5 H), 7.17 (s, 1H), 4.15 (s, 2 H), 2.42 (s, 3 H); Analysis for C$_{13}$H$_{11}$ClOS$_2$: Calcd: C, 55.21; H, 3.92. Found: C, 55.34; H, 3.96.

Step 2. 3-Acetyl-5-chloro-2-thiophenesulfonamide (3)

Chlorine gas was bubbled into a stirred, 2° to 10° C. solution of 3-acetyl-5-chloro-2-(benzylthio)thiophene (2, 1 kg, 3.53 mol) in ethyl acetate (20 L) until TLC analysis indicated consumption of starting material. The solution was purged with a vigorous stream of air for 1 hour before ammonia was bubbled in, keeping the temperature between 5° and 15° C. This was continued until TLC analysis indicated consumption of the intermediate sulfenyl chloride. The mixture was again purged with air for 1 hour before water (5 L) was added and the solution was cooled to 15° C. Sodium tungstate dihydrate (0.5 eq, 1.77 mol, 583 g) was added followed by the addition of 30% hydrogen peroxide (8 L) over 5 minutes. The mixture was heated at 35° C. for 2 hours and then stirred at ambient temperature for 16 hours before water (5 L) was added and the phases were split. Water (5 L) was added to the organic phase followed by solid sodium bisulfite until a negative test for peroxide was obtained with peroxide test paper. The phases were split and the organic phase was washed first with saturated aqueous sodium bicarbonate until the pH of the wash was 8, then with saturated aqueous sodium chloride, dried over sodium sulfate, filtered, and stripped of solvent by rotary evaporation. The residual semi-solid was triturated with t-butyl methyl ether and the solid was collected by filtration, washed with t-butyl methyl ether, and dried in air to a constant weight of 597 grams (71%) of 3: mp 178°–179° C.; IR (KBr) 3340, 3260, 3089, 1682, 1553, 1508, 1403, 1360, 1224, 1153 cm$^{-1}$; $^1$H NMR (DMSO-d$_6$) $\delta$7.72 (s, 2 H), 7.70 (s, 1H), 2.55 (s, 3 H); Analysis for C$_6$H$_6$ClNO$_3$S$_2$: Calcd: C, 30.06; H, 2.52; N, 5.84; S, 26.75. Found: C, 30.19; H, 2.51; N, 5.80; S, 26.70.

Step 3. 3-Bromoacetyl-5-chloro-2-thiophenesulfonamide (4)

A 50-L, 5-necked flask equipped with a mechanical stirrer, a thermometer, and a 1-L addition funnel was charged with 3-acetyl-5-chloro-2-thiophenesulfonamide (3, 1.087 kg, 4.55 mol) and ethyl acetate (22 L). The pale yellow suspension was cooled to 1° C. over 45 minutes using an ice-water bath, and 90% pyridinium bromide perbromide (1.305 kg, 3.67 mol) was added in one portion. Sulfuric acid (544 mL) was added via the addition funnel over 10 minutes causing the temperature to rise to 5° C. The reaction mixture was stirred for 1 hour, after which TLC analysis indicated complete reaction. Thirty minutes later, water (5 L) was added and the mixture was stirred for 5 minutes before the phases were split. The organic phase was washed with saturated aqueous sodium chloride until the pH of the wash was 3 (4×5 L required), dried over sodium sulfate (1 kg), filtered, and stripped of solvent by rotary evaporation. The residue was triturated with methylene chloride (2 L) and chilled for 15 minutes before the solid was collected by filtration, washed with cold methylene chloride (2 L), and dried in air at ambient temperature to a constant weight of 1.041 kilograms (72%) of 4: mp 147°–148° C.; IR (KBr) 3381, 3263, 3093, 1694, 1532, 1403, 1336, 1163, 1102 cm$^{-1}$; $^1$H NMR (acetone-d$_6$) $\delta$7.76 (s, 1 H), 7.11 (br, 2 H), 4.76 (s, 2 H); Analysis for C$_6$H$_5$BrClNO$_3$S$_2$: Calcd: C, 22.62; H, 1.58; N, 4.40; S, 20.13. Found: C, 22.66; H, 1.60; N, 4.35; S, 20.12.

Step 4. (S)-3,4-Dihydro-6-chloro-4-hydroxy-4H-thieno[3,2-e]-1,2-thiazine-1,1-dioxide (5)

A 50-L, 5-necked flask equipped with a mechanical stirrer and a thermometer was flushed with nitrogen overnight. Working under nitrogen, the flask was charged with 3-bromoacetyl-5-chloro-2-thiophenesulfonamide (4, 855 g, 2.68 mol) and t-butyl methyl ether (12.5 L). The stirred suspension was cooled to −40° C. using a dry-ice/2-propanol bath and (+)-$\beta$-chlorodiisopinocampheylborane (4.5 L of a 1.2M solution in t-butyl methyl ether, 5.4 mol, 2 eq) was added via a cannula over 30 minutes, causing the temperature to rise to −32° C. The reaction mixture was maintained between −25° to −20° C. for 3.5 hours, after which TLC analysis indicated complete reduction. The mixture was warmed to 0° C. and 1M aqueous sodium hydroxide (11 L) was added from an addition funnel over 10 minutes, causing the temperature to rise to 22° C. The biphasic mixture was stirred vigorously at ambient temperature for 2 hours, after which TLC analysis indicated complete cyclization. The phases were split and the dark aqueous layer was extracted with t-butyl methyl ether (3 L), acidified to pH 1 using concentrated hydrochloric acid, and extracted with ethyl acetate (2×4 L). The combined ethyl acetate extracts were washed with saturated aqueous sodium chloride (3 L), dried over sodium sulfate (1 kg), filtered, and concentrated to a volume of about 1 liter by rotary evaporation, at which point toluene (2 L) was added. As the remainder of the ethyl acetate was stripped, the product crystallized from toluene. It was collected by filtration, washed with toluene (2 L) and methylene chloride (2 L), and dried in air at ambient temperature to a constant weight of 498 grams (77%) of 5: mp 126°–127° C.; IR (KBr) 3550, 3230, 1430, 1410, 1320, 1170, 860, 720, 550, 470 cm$^{-1}$; $^1$H NMR (DMSO-d$_6$) $\delta$8.18-8.11 (m, 1H), 7.19 (s, 1H), 5.8 (br, 1 H), 4.60-4.54 (m, 1 H), 3.68-3.55 (m, 1 H), 3.50-3.35 (m, 1 H); [$\alpha$]$^{25}_D$ −5.9° (c=1, CH$_3$OH); Analysis for C$_6$H$_6$ClNO$_3$S$_2$: Calcd: C, 30.06; H, 2.52; N, 5.84. Found: C, 30.14; H, 2.56; N, 5.80.

EXAMPLE 2

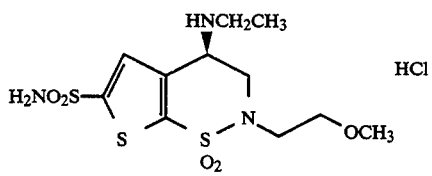

(R)-3,4-Dihydro-4-ethylamino-2-(2-methoxyethyl)-4H-thieno[3,2-e]-1,2-thiazine-6-sulfonamide-1,1-dioxide Hydrochloride Step 1. (S)-3,4-Dihydro-6-chloro-4-hydroxy-2-(2-methoxyethyl)-4H-thieno[3,2-e]-1,2-thiazine-1,1-dioxide (6, $R_3$=CH$_2$CH$_2$OCH$_3$)

A mixture of (S)-3,4-dihydro-6-chloro-4-hydroxy-4H-thieno[3,2-e]-1,2-thiazine-1,1-dioxide (5, 1.2 g) and potassium carbonate (2.1 g) in dimethylsulfoxide (7 mL) was treated with 1-bromo-2-methoxyethane (0.5 eq, 0.25 mL) and the mixture was stirred at ambient temperature for 3 hours. Another 0.25 mL of 1-bromo-2-methoxyethane was then added and the mixture was stirred at ambient temperature for 18 hours. TLC analysis after this period indicated incomplete reaction, so another 0.25 mL of 1-bromo-2-methoxyethane was added and the mixture was stirred at ambient temperature for another 3 hours. At this point, TLC indicated complete reaction. The mixture was poured into saturated aqueous sodium chloride (50 mL) and extracted with t-butyl methyl ether. The organic phase was washed sequentially with 10% aqueous sodium hydroxide, 1:1 5.25% sodium hypochlorite/water, and saturated aqueous sodium chloride, dried over sodium sulfate, and stripped of solvent by rotary evaporation. Residual solvent was removed under vacuum to provide 1.1 grams (75%) of (S)-3,4-dihydro-6-chloro-4-hydroxy-2-(2-methoxyethyl)-4H-thieno[3,2-e]-1,2-thiazine-1,1-dioxide as a light yellow oil: IR (film) 3500-3400, 1430, 1340, 1170, 1120, 1080, 1040, 700 cm$^{-1}$; $^1$H NMR (CDCl$_3$) δ6.98 (s; 1H), 4.57 (br, 1 H), 4.33 (dd, 1 H, J=4 and 16 Hz), 4.16 (br, 1 H), 3.91-3.38 (m, 5 H), 3.31 (s, 3 H); $[\alpha]^{25}_D$ +4.0° (c=1, CH$_3$OH); Analysis for C$_9$H$_{12}$ClNO$_4$S$_2$: Calcd: C, 36.30; H, 4.06; N, 4.70. Found: C, 36.23; H, 4.05; N, 4.66.

Step 2. (S)-3,4-Dihydro-4-hydroxy-2-(2-methoxyethyl)-4H-thieno[3,2-e]-1,2-thiazine-6-sulfonamide-1,1-dioxide (7, $R_3$=CH$_2$CH$_2$OCH$_3$)

Working under nitrogen, n-butyllithium (3.0 L of a 2.5M hexane solution) was added dropwise to a stirred, −70° to −60° C. solution of (S)-3,4-dihydro-6-chloro-4-hydroxy-2-(2-methoxyethyl)-4H-thieno[3,2-e]-1,2-thiazine-1,1-dioxide (0.87 kg) in anhydrous tetrahydrofuran (24.8 L) over 1.75 hours. The resulting mixture was stirred at −70° C. for 1.5 hours before sulfur dioxide gas was bubbled in until the pH of the mixture was 3-4. The mixture was then allowed to warm to 20° C. overnight. The solvent was removed at reduced pressure on a rotary evaporator and the residue was taken up in water (4 L). The solution was added in one portion to a solution of sodium acetate trihydrate (2.714 kg) and hydroxylamine-O-sulfonic acid (1.515 kg) in water (15 L) and the mixture was stirred at room temperature for 15 h. The pH was adjusted to 8-9 using 50% aqueous sodium hydroxide (1 L) and solid sodium bicarbonate (ca. 500 g) and the mixture was extracted with ethyl acetate (1×8 L plus 2×4 L). The combined extracts were washed with aqueous sodium bicarbonate (500 g in 5 L) and saturated aqueous sodium chloride, dried over magnesium sulfate, and stripped of solvent to leave an oil. The residual oil was triturated with methylene chloride (3 L) until crystallization occurred. After chilling in ice, the solid was collected by filtration, washed with methylene chloride (2×1 L), and dried in air at ambient temperature to a constant weight of 0.763 kilograms (67%) of (S)-3,4-dihydro-4-hydroxy-2-(2-methoxyethyl)-4H-thieno[3,2-e]-1,2-thiazine-6-sulfonamide-1,1-dioxide: mp 131°-133° C.; $^1$H NMR (DMSO-d$_6$) δ8.03 (br s, 2 H), 7.58 (s, 1 H), 6.14 (d, 1 H, J=6 Hz), 4.88-4.80 (m, 1 H), 3.95 (dd, 1 H, J=5, 15 Hz), 3.78 (dd, 1 H, J=6, 15 Hz), 3.54-3.36 (m, 4 H), 3.26 (s, 3 H); IR (KBr) 3508, 3347, 3248, 1348, 1170, 1112, 658, 611, 567 cm$^{-1}$; $[\alpha]^{25}_D$ −0.7° (c=1, CH$_3$OH); Analysis for C$_9$H$_{14}$N$_2$O$_6$S$_3$: Calcd: C, 31.57; H, 4.12; N, 8.18. Found: C, 31.75; H, 4.20; N, 8.07.

Step 3. (R)-3,4-Dihydro-4-ethylamino-2-(2-methoxyethyl)-4H-thieno[3,2-e]-1,2-thiazine-6-sulfonamide-1,1-dioxide Hydrochloride A solution of (S)-3,4-dihydro-4-hydroxy-2-(2-methoxyethyl)-4H-thieno[3,2e]-1,2-thiazine-6-sulfonamide-1,1-dioxide (0.742 kg) and trimethyl orthoacetate (0.607 L) in acetonitrile (7.42 L) was refluxed for 16 hours. The solvent was removed by rotary evaporation leaving the methoxyimidate as a viscous oil. The oil was dissolved in anhydrous tetrahydrofuran (4 L) and transferred back to the original 22-L reaction flask. The solution was cooled to 8° C. and triethylamine (0.756 L) and p-toluenesulfonyl chloride (1.034 kg) were added sequentially causing the temperature to rise to 18° C. TLC analysis after 1 hour indicated complete reaction. The mixture was cooled to 0° C. and 70% aqueous ethylamine (6.145 L) was added over 65 minutes while the temperature was kept below 12° C. The mixture was stirred at 20° C. for 60 hours before the volatiles were removed by rotary evaporation and the residue was partitioned between 1M aqueous hydrochloric acid (8 L) and a mixture of ethyl acetate (4 L) and diethyl ether (4 L). The organic layer was removed and extracted with 1M aqueous hydrochloric acid (2×2 L) and the combined acid aqueous phases were adjusted to pH 13-14 using 50% aqueous sodium hydroxide. The basic solution was washed with diethyl ether (2 L), adjusted to pH 7-8 using concentrated hydrochloric acid and sodium bicarbonate, and extracted with ethyl acetate (4×2 L). The combined ethyl acetate extracts were washed with aqueous sodium chloride, dried over magnesium sulfate, and filtered. The filtrate was returned to the 22-L flask and hydrogen chloride was bubbled into the stirred solution until the pH was 1-2. A gummy oil separated that crystallized with time. The mixture was chilled and the solid was collected by filtration, washing with ethyl acetate (2 L) and diethyl ether (1 L). The material was dried in air at ambient temperature to a constant weight of 441.5 grams (50%) of (R)-3,4-dihydro-4-ethylamino-2-(2-methoxyethyl)-4H-thieno[3,2-e]-1,2-thiazine-6-sulfonamide-1,1-dioxide hydrochloride. Material recrystallized from methanol/ethyl acetate had the following characteristics: mp 225°-228° C.; $^1$H NMR (DMSO-d$_6$) δ10 (br s, 2 H), 8.2 (s, 3 H), 4.9 (s, 1 H), 4.2 (m, 2 H), 3.5 (m, 4 H), 3.26 (s, 3 H), 3.05 (br s, 2 H), 1.27 (t, 3 H); IR (KBr) 3291, 3127, 3014, 2987, 2946, 1353, 1328 1160, 1108, 1016, 926 cm$^{-1}$; $[\alpha]^{25}_{312.6}$ −49.1° (c=1, H$_2$O); Analysis for C$_{11}$H$_{20}$ClN$_3$O$_6$S$_3$: Calcd: C, 32.62; H, 4.73; N, 10.38. Found: C, 32.62; H, 4.93; N, 10.31.

EXAMPLE 3

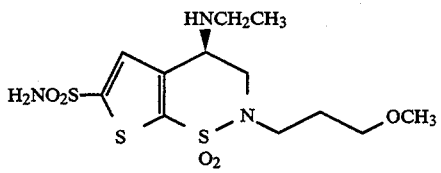

(R)-3,4-Dihydro-4-ethylamino-2-(3-methoxypropyl)-2H-thieno[3,2-e]-1,2-thiazine-6-sulfonamide-1,1-dioxide Step 1. (S)-3,4-Dihydro-6-chloro-4-hydroxy-2-(3-methoxypropyl)-4H-thieno[3,2-e]-1,2-thiazine-1,1-dioxide (6, $R_3=CH_2CH_2CH_2OCH_3$)

A 5-L, 4-necked flask equipped with a mechanical stirrer, a thermometer, and a 250-mL addition funnel was charged with (S)-3,4-dihydro-6-chloro-4-hydroxy-4H-thieno[3,2-e]-1,2-thiazine-1,1-dioxide (5, 350 g, 1.46 mol), dimethylsulfoxide (1.75 L), and potassium carbonate (605 g, 4.38 mol). 1-Bromo-3-methoxypropane (268 g, 1.75 mol, 1.2 eq) was added via the addition funnel in eight equal portions spaced 1 hour apart. Each addition caused a small rise in temperature, amounting to a 10° C. increase over 8 hours. TLC analysis 1.5 hours after the final addition indicated complete reaction. The reaction mixture was poured into a 50-L flask equipped with a mechanical stirrer containing saturated aqueous sodium chloride (18 L). The original reaction vessel was rinsed with both water and t-butyl methyl ether. The aqueous solution was extracted with t-butyl methyl ether (2×4 L) and the combined extracts were washed with 1M aqueous sodium hydroxide (2 L), 1:1 bleach/water (2 L), and saturated aqueous sodium chloride (2 L). The t-butyl methyl ether solution was dried over sodium sulfate (500 g), filtered, and stripped of solvent by rotary evaporation. The residual oil was transferred to a 2-L flask and trace solvent was removed by rotary evaporation at 50° C., first under water aspirator, then under high vacuum for 6 hours to provide 427 grams (94%) of (S)-3,4-dihydro-6-chloro-4-hydroxy-2-(3-methoxypropyl)-4H-thieno[3,2-e]-1,2-thiazine-1,1-dioxide as a light yellow syrup: IR (film) 3500, 2931, 2878, 1422, 1336, 1167, 1114, 1071, 1028, 690 cm$^{-1}$; $^1$H NMR (CDCl$_3$) $\delta$6.96 (s, 1 H), 4.64 (br s, 1 H), 4.08 (dd, 1 H, J=4 and 15 Hz), 3.81-3.28 (m, 6 H), 3.25 (s, 3 H), 2.04-1.83 (m, 2 H); $[\alpha]^{25}_D$ +11.4° (c=1, CH$_3$OH); Analysis for C$_{10}$H$_{14}$ClNO$_4$S$_2$: Calcd: C, 38.52; H, 4.53; N, 4.49. Found: C, 38.65; H, 4.54; N, 4.47.

Step 2. (S)-3,4-Dihydro-4-hydroxy-2-(3-methoxypropyl)-4H-thieno[3,2-e]-1,2-thiazine-6-sulfonamide-1,1-dioxide (7, $R_3=CH_2CH_2CH_2OCH_3$)

A 50-L flask equipped with an addition funnel, a thermometer, and a mechanical stirrer was purged with nitrogen for 15 hours and then charged with (S)-3,4-dihydro-6-chloro-4-hydroxy-2-(3-methoxypropyl)-4H-thieno[3,2-e]-1,2-thiazine-1,1-dioxide (1.065 kg, 3.42 mol) in anhydrous tetrahydrofuran (27 L). The solution was chilled to −70° C. using a dry-ice/i-propanol bath and n-butyllithium (7.7 mol, 2.3 eq, 3.08 L of a 2.5M hexane solution) was added dropwise over 2.5 hours while the temperature was maintained below −66° C. After 1 hour, sulfur dioxide was introduced into the mixture until it was acidic (pH 4). The mixture was allowed to warm to ambient temperature overnight before the solvent was removed by rotary evaporation. The residue was dissolved in water (5 L) and the solution was added in one portion to a 0° C. solution of sodium acetate trihydrate (2.796 kg, 20.5 mol) and hydroxylamine-O-sulfonic acid (1.549 kg, 13.7 mol) in water (6 L) causing the temperature to rise to 25° C. After stirring for 15 hour at ambient temperature, the solution was extracted with ethyl acetate (3×4 L). The combined extracts were washed first with saturated aqueous sodium bicarbonate until the wash was basic, then saturated aqueous sodium chloride, dried over sodium sulfate, filtered, and concentrated on the rotary evaporator. Methylene chloride (6 L) was added to the residual oil along with with 5 grams of seed crystals and the mixture was chilled and agitated with a spatula to induce crystallization. The solid was collected by filtration, washed with methylene chloride, and dried in air at ambient temperature to a constant weight of 748 grams (61%) of (S)-3,4-dihydro-4-hydroxy-2-(3-methoxypropyl)-4H-thieno[3,2-e]-1,2-thiazine-6-sulfonamide-1,1-dioxide: mp 111°-113° C.; IR (KBr) 3384, 3224, 3095, 1357, 1341, 1301, 1170, 1122, 1086, 942, 690, 616, 567 cm$^{-1}$; $^1$H NMR (DMSO-d$_6$) $\delta$8.05 (s, 2 H), 7.59 (s, 1 H), 6.15 (d, 1 H, J=6 Hz), 4.86-4.78 (m, 1 H), 3.92 (dd, 1 H, J=4.5 and 15 Hz), 3.73 (dd, 1 H, J=5.6 and 15 Hz), 3.39-3.28 (m, 4 H), 3.21 (s, 3 H), 1.88-1.75 (m, 2 H); $[\alpha]^{25}_{312.5}$ +264° (c=1, CH$_3$OH); Analysis for C$_{10}$H$_{16}$ClN$_2$O$_6$S$_3$: Calcd; C, 33.69; H, 4.53; N, 7.86. Found: C, 33.61; H, 4.55; N, 7.77.

Step 3. (R)-3,4-Dihydro-4-ethylamino-2-(3-methoxypropyl)-4H-thieno[3,2-e]-1,2-thiazine-6-sulfonamide-1,1-dioxide A 500-mL flask equipped with a reflux condenser was charged with (S)-3,4-dihydro-4-hydroxy-2-(3-methoxypropyl)-4H-thieno[3,2-e]-1,2-thiazine-6-sulfonamide-1,1-dioxide (28.5 g, 0.08 mol), acetonitrile (285 mL), and trimethylorthoacetate (23.4 mL, 0.184 mol). The mixture was heated at reflux (85° C.) for 16 hours, after which TLC analysis indicated complete reaction. After cooling for 1 hour, the solvent was removed by rotary evaporation. The residual oil was dissolved in anhydrous tetrahydrofuran (150 mL) and the solution was transferred to a 1-L, 3-necked flask equipped with a thermometer, an addition funnel, and a nitrogen inlet. The solution was cooled to 4° C. under nitrogen and triethylamine (24.5 mL, 0.176 mol) and p-toluenesulfonyl chloride (30.5 g, 0.160 mol) were added sequentially. A precipitate was observed within 5 minutes. The mixture was stirred at 4° to 7° C. for 2 hours, after which TLC analysis indicated complete tosylation. 70% Aqueous ethylamine (260 mL, 2.80 mol) was added dropwise over 30 minutes while the temperature was kept below 15° C. The mixture was stirred at ambient temperature for 18.5 hours before the solution was cooled to 5° C. and concentrated hydrochloric acid (280 mL) was added dropwise over 1 hour while the temperature was kept below 30° C. The solution was extracted with diethyl ether (2×250 mL) and the combined extracts were back extracted with 1M aqueous hydrochloric acid (200 mL). The pH of the aqueous phase was adjusted to 8 using solid sodium bicarbonate causing a white solid to precipitate. After chilling for 2 hour, the solid was collected by filtration and washed with water. TLC analysis of the filtrate indicated that some product was present, so the filtrate was extracted with ethyl acetate. This and additional ethyl acetate was used to dissolve the filter cake and the solution was dried over magnesium sulfate, filtered, stripped of solvent, and dried to a constant weight of 24.0 grams (78%) of crude (R)-3,4-dihydro-4-ethylamino-2-(3-methoxypropyl)-4H-thieno[3,2-e]-1,2-thiazine-6-sulfonamide-1,1-dioxide. Material recrystallized from 2-propanol had the following characteristics: mp 125°–127° C.; IR (KBr) 3313, 1355, 1336, 1174, 1156, 1080, 1015, 914, 904, 652 cm$^{-1}$; $^1$H NMR (DMSO-d$_6$) δ8.01 (s, 2 H), 7.65 (s, 1 H), 4.10-4.03 (m, 1 H), 3.87-3.76 (m, 2 H), 3.47-3.33 (m, 4 H), 3.22 (s, 3 H) partially overlapped by 3.20-3.09 (m, 1 H), 2.59-2.49 (m, 2 H), 1.86-1.74 (m, 2 H), 1.01 (t 3 H J=7 Hz); [α]$^{25}$312.6 −26.1° (c=1, pH 3 citric acid buffer); Analysis for C$_{12}$H$_{21}$N$_3$O$_5$S$_3$: Calcd: C, 37.58; H, 5.48; N, 10.96. Found: C, 37.66; H, 5.56; N, 10.98.

EXAMPLE 4

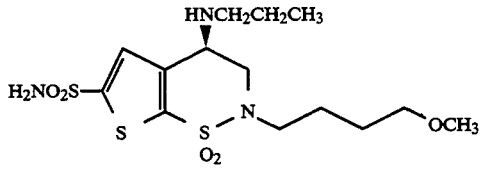

(R)-3,4-Dihydro-2-(4-methoxybutyl)-4-propylamino-4H-thieno[3,2-e]-1,2-thiazine-6-sulfonamide-1,1-dioxide Step 1. (S)-3,4-Dihydro-6-chloro-4-hydroxy-2-(4-methoxybutyl)-4H-thieno[3,2-e]-1,2-thiazine-1,1-dioxide (6, R$_3$=CH$_2$CH$_2$CH$_2$CH$_2$OCH$_3$)

A mixture of (S)-3,4-dihydro-6-chloro-4-hydroxy-4H-thieno[3,2-e]-1,2-thiazine-1,1-dioxide (5, 65.4 g) and potassium carbonate (113.3 g) in dimethylsulfoxide (350 mL) was treated with 1-bromo-4-methoxybutane (20.6 g) and the mixture was stirred at ambient temperature for 4 hours. Another 20.6 grams of 1-bromo-4-methoxybutane was then added and the mixture was stirred at ambient temperature for 18 hours. TLC analysis after this period indicated incomplete reaction, so another 4.6 grams of 1-bromo-4-methoxybutane was added and the mixture was stirred at ambient temperature for another 3 hours. At this point, TLC indicated complete reaction. The mixture was poured into saturated aqueous sodium chloride (1 L) and extracted with diethyl ether (3×150 mL). The organic phase was washed sequentially with 100 mL each of 10% aqueous sodium hydroxide, 1:1 5.25% sodium hypochlorite/water, and saturated aqueous sodium chloride, dried over sodium sulfate, and stripped of solvent by rotary evaporation. Residual solvent was removed under vacuum to provide 82 grams (92%) of (S)-3,4-dihydro-6-chloro-4-hydroxy-2-(4-methoxybutyl)-4H-thieno[3,2-e]-1,2-thiazine-1,1-dioxide as a light yellow oil: IR (film) 3500, 3350, 3070, 2950, 2850, 1525, 1480, 1440, 1380, 1330, 1160, 1120, 1080, 1020, 1100 cm$^{-1}$; [α]$^{25}$$_D$+11.4° (c=1.1, methanol); Anal. Calcd for C$_{11}$H$_{16}$ClNO$_4$S$_2$: C, 40.55; H, 4.95; N, 4.30. Found: C, 40.47; H, 4.99; N, 4.27.

Step 2. (S)-3,4-Dihydro-6-chloro-4-hydroxy-2-(4-methoxybutyl)-4H-thieno[3,2-e]-1,2-thiazine-6-sulfonamide-1,1-dioxide (7, R$_3$=CH$_2$CH$_2$CH$_2$CH$_2$OCH$_3$)

Working under nitrogen, n-butyllithium (250 mL of a 2.5M hexane solution) was added dropwise to a stirred, −78° to −60° C. solution of (S)-3,4-dihydro-6-chloro-4-hydroxy-2-(4-methoxybutyl)-4H-thieno[3,2-e]-1,2-thiazine-1,1-dioxide (76.6 g) in anhydrous tetrahydrofuran (1.4 L) over 30 minutes. After 1 hour at −78° to −60° C., sulfur dioxide was introduced above the solution over 30 minutes at a temperature of −70° to −50° C. until the pH was 4. After 2.5 hours at −60° C., the solution was stripped of volatiles at reduced pressure and the residual orange oil was dissolved in water (500 mL). The solution was added in one portion to a 0° C. solution of hydroxylamine-O-sulfonic acid (113 g) and sodium acetate trihydrate (200 g) in water (1.5 L). The mixture was stirred at ambient temperature overnight before it was extracted with ethyl acetate (3×500 mL). The combined ethyl acetate extracts were washed with saturated aqueous sodium bicarbonate to pH 9, water, and saturated aqueous sodium chloride, dried over sodium sulfate, and stripped of solvent by rotary evaporation. The residual oil was dissolved in methylene chloride (200 mL) and some seed crystals were added. After 1 hour, the solid that separated was collected by filtration, washed with methylene chloride, and dried in air to a constant weight of 61.4 grams (71%) of (S)-3,4-dihydro-6-chloro-4-hydroxy-2-(4-methoxybutyl)-4H-thieno[3,2-e]-1,2-thiazine-6-sulfonamide-1,1-dioxide: mp 109°–111° C.; IR (KBr) 3500, 3350, 3200, 3100, 2990, 2985, 2965, 2950, 2940, 2935, 2910, 1530, 1455, 1435, 1400-1300, 1235, 1220, 1170, 1160, 1140, 1110, 1080 cm$^{-1}$; [α]$^{25}$$_D$+1.8° (c=1.0, methanol); Anal. Calcd for C$_{11}$H$_{18}$N$_2$O$_6$S$_3$: C, 35.66; H, 4.90; N, 7.56. Found: C, 35.91; H, 4.87; N, 7.52.

Step 3. (R)-3,4-Dihydro-2-(4-methoxybutyl)-4-propylamino-4H-thieno[3,2-e]-1,2-thiazine-6-sulfonamide-1,1-dioxide A solution of (S)-3,4-dihydro-6-chloro-4-hydroxy-2-(4-methoxybutyl)-4H-thieno[3,2-e]-1,2-thiazine-6-sulfonamide-1,1-dioxide (30 g) and trimethyl orthoacetate (16 mL) in acetonitrile (300 mL) was refluxed for 18 hours. TLC analysis indicated incomplete reaction, so another 2 equivalents of trimethyl orthoacetate were added and reflux continued for 18 hours. Again, TLC analysis indicated incomplete reaction, so another 1 equivalent of trimethyl orthoacetate was added and reflux continued for 5 hours. As the reaction was judged to be complete at this point, the volatiles were removed by rotary evaporation. The residual oil was dissolved in anhydrous tetrahydrofuran (150 mL) and the solution was cooled to −5° C. under nitrogen. Triethylamine (25 mL) and p-toluenesulfonyl chloride (30.8 g) were added sequentially causing the temperature to rise to 5° C. over 10 minutes. The reaction mixture was stirred at 0° C. for 1 hour before a mixture of n-propylamine (200 mL) and water (85 mL) was added. The addition caused the temperature to rise to 15° C. and required 1.5 hours. The resulting solution was stirred at ambient temperature for 18 hours before it was cooled to 5° C. and acidified to pH 0-1 by the slow addition of concentrated hydrochloric acid (250 mL). The solution was extracted with diethyl ether (2×300 mL) and the combined extracts were back-extracted with 1M aqueous hydrochloric acid (150 mL). The combined aqueous phases were neutralized to pH 8 using solid sodium bicarbonate resulting in a white precipitate. After 1 hour, the solid was collected by filtration, washed with water, and dried in air to a constant weight of 19.7 grams (59%) of crude (R)-3,4-dihydro-2-(4-methoxybutyl)-4-propylamino-4H-thieno[3,2-e]-1,2-thiazine-6-sulfonamide-1,1-dioxide. Material recrystallized from 2-propanol had the following characteristics: mp 151°–152° C.; $^1$H NMR (CDCl$_3$/DMSO-d$_6$) δ7.6 (s, 1H), 7.2 (br s, 3 H), 3.95 (m, 1 H), 3.85 (m, 2 H), 3.45 (m, 4 H), 3.33 (s, 3 H), 2.7 (m, 2 H), 1.7 (br m, 4 H), 1.5 (m, 2 H) 0.95 (t 3 H); $[\alpha]^{25}_D$ +17.9° (c=1.0, methanol).
We claim:
1. A compound of the formula
2. A compound of the formula
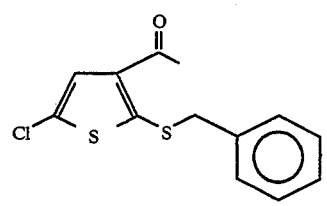
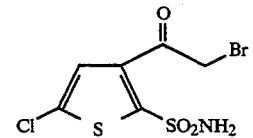
* * * * *

UNITED STATES PATENT AND TRADEMARK OFFICE
CERTIFICATE OF CORRECTION

PATENT NO. : 5,424,448
DATED : June 13, 1995
INVENTOR(S) : Dean, et al.

It is certified that error appears in the above-indentified patent and that said Letters Patent is hereby corrected as shown below:

Column 3, line 40, change "(+)-β-" to [(+)-B-].

Column 4, line 12, change "pseudourea" to [pseudothiourea].

Column 5, line 14, change "-β-" to [-B-].

Column 5, line 24, change "-β-" to [-B-].

Column 8, line 34, change "-β-" to [-B-].

Signed and Sealed this

Twenty-third Day of April, 1996

BRUCE LEHMAN

*Attest:*

*Attesting Officer*       *Commissioner of Patents and Trademarks*